United States Patent [19]

Magee et al.

[11] 4,219,805
[45] Aug. 26, 1980

[54] LUBRICATING OIL DEBRIS MONITORING SYSTEM

[75] Inventors: James H. Magee; Thomas E. Tauber, both of Glenolden, Pa.

[73] Assignee: Technical Development Company, Glenolden, Pa.

[21] Appl. No.: 950,972

[22] Filed: Oct. 13, 1978

[51] Int. Cl.² ............................................. G01R 27/02
[52] U.S. Cl. .................................... 340/631; 324/204
[58] Field of Search ...................... 340/627, 631, 607; 73/10, 64; 324/204

[56] References Cited

U.S. PATENT DOCUMENTS

| 3,432,750 | 3/1969 | Botstiber | 324/204 |
| 3,748,576 | 7/1973 | Sigournay | 340/631 |
| 3,878,103 | 4/1975 | Miller et al. | 340/631 |
| 4,030,028 | 6/1977 | Allender | 340/631 |
| 4,070,660 | 1/1978 | Tauber | 340/631 |
| 4,100,491 | 7/1978 | Newman, Jr. et al. | 324/204 |
| 4,127,808 | 11/1978 | Sproul et al. | 340/631 |

*Primary Examiner*—Gerald L. Brigance
*Attorney, Agent, or Firm*—Robert S. Lipton; Arthur E. Oaks

[57] ABSTRACT

An electromagnetic system is provided to capture ferrous particles in a circulating fluid medium and provide analog and digital data which relate both to the mass of any significant individual particles captured and the total mass of such particles accumulated in a given time for subsequent retrieval. A periodic self checking capability is also included to determine if the system is functioning normally.

13 Claims, 6 Drawing Figures

LUBRICATING OIL DEBRIS MONITORING SYSTEM

BACKGROUND OF THE INVENTION

There are numerous situations wherein a fluid medium is contaminated by particulate substances, especially ferrous particles. Frequently it is desired to determine the presence of such substances. Data are generally acquired which indicates the presence of particles. The data are used either as an indication of the condition of the fluid which in turn may serve as an indication of a possible maintenance problem with the apparatus being served by the fluid. Of course, the data may be used to monitor the condition of the fluid itself. In highly critical applications such as in the lubricating of helicopter and aircraft engines and transmissions, where the opportunities for maintenance may be quite limited, it is further desirable to be able to discriminate between minor particles ("fuzz") resulting from normal wear and larger individual particles indicative of abnormal conditions, such as cracks or impending fatigue failure. Lastly, it is very desirable that the observer or pilot be able to distinguish between random occurrences of individual particles and a steady buildup of such particles, that is, to measure the rate of particle accumulation.

A great number of devices have been developed to filter or trap loose particles in engine coolant and/or lubrication systems. In many of the devices designed for ferrous particles, such as those described by Lammers in U.S. Pat. No. 3,421,627 and Tauber in U.S. Pat. No. 3,753,442, this is done by attracting the particles to the poles of a magnet. In more advanced versions of these devices, such as those described by Botstiber in U.S. Pat. Nos. 2,983,890 and 3,317,042, the magnet is combined with a signaling device designed to indicate the presence of either a significantly large particle or a large collection of smaller particles. This acts to warn the pilot of a possible impending failure in time for corrective repairs to be applied. However, these devices provide no information as to whether the source of the signal is an innocuous accumulation of normal wear fuzz, a large random sliver formed by or introduced during some previous maintenance operation or an accumulation of 100+ micron particles which have been found to be highly significant indicators of crack formation and growth. Furthermore, such devices provide no information as to the rate of particle accumulation so it is not really possible for the user either to assess the significance of the warning signal or to estimate with any reliability the remaining useful lifetime of the system.

SUMMARY OF THE INVENTION

The present invention, like those of the prior art, uses magnetic attraction to capture ferrous particles circulating in the system. However, unlike these devices, each of the particles so captured is used to actuate the generation of a signal pulse on capture, the amplitude and decay characteristics of which are essentially proportional to the mass of the individual particles trapped. These signal parameters, after discrimination by suitable logic circuitry, can be converted to both analog and digital values which, if deemed to be significant, are accumulated and displayed to an observer to show not only particle capture but also to provide both an indication of the significance of each individual particle so captured and a measure of total quantity of debris accumulated. Furthermore, by monitoring the time to reach a predetermined mass of such "significant" particles on the magnet, it is possible to compute the rate of accumulation thus allowing an assessment of residual system utility and scheduling of maintenance before a complete breakdown may occur.

It is therefore a principal object of the present invention to provide a ferrous particle capturing device for use in circulating liquid systems wherein the mass of the individual particles so captured is measured.

It is a further object of this invention to provide signals suitable for analog and digital display which are a function of the mass of the captured particles, for the estimation of both individual particle size and total amount of material accumulated.

It is still a further object of the present invention to provide a means by which the rate of particulate accumulation can be measured for a more positive assessment of the system damage.

Other and further objects of this invention will become apparent to those skilled in the art upon consideration of the following specification when read in conjunction with the attached drawings.

DESCRIPTION OF THE PREFERRED EMBODIMENT

Figure 1:
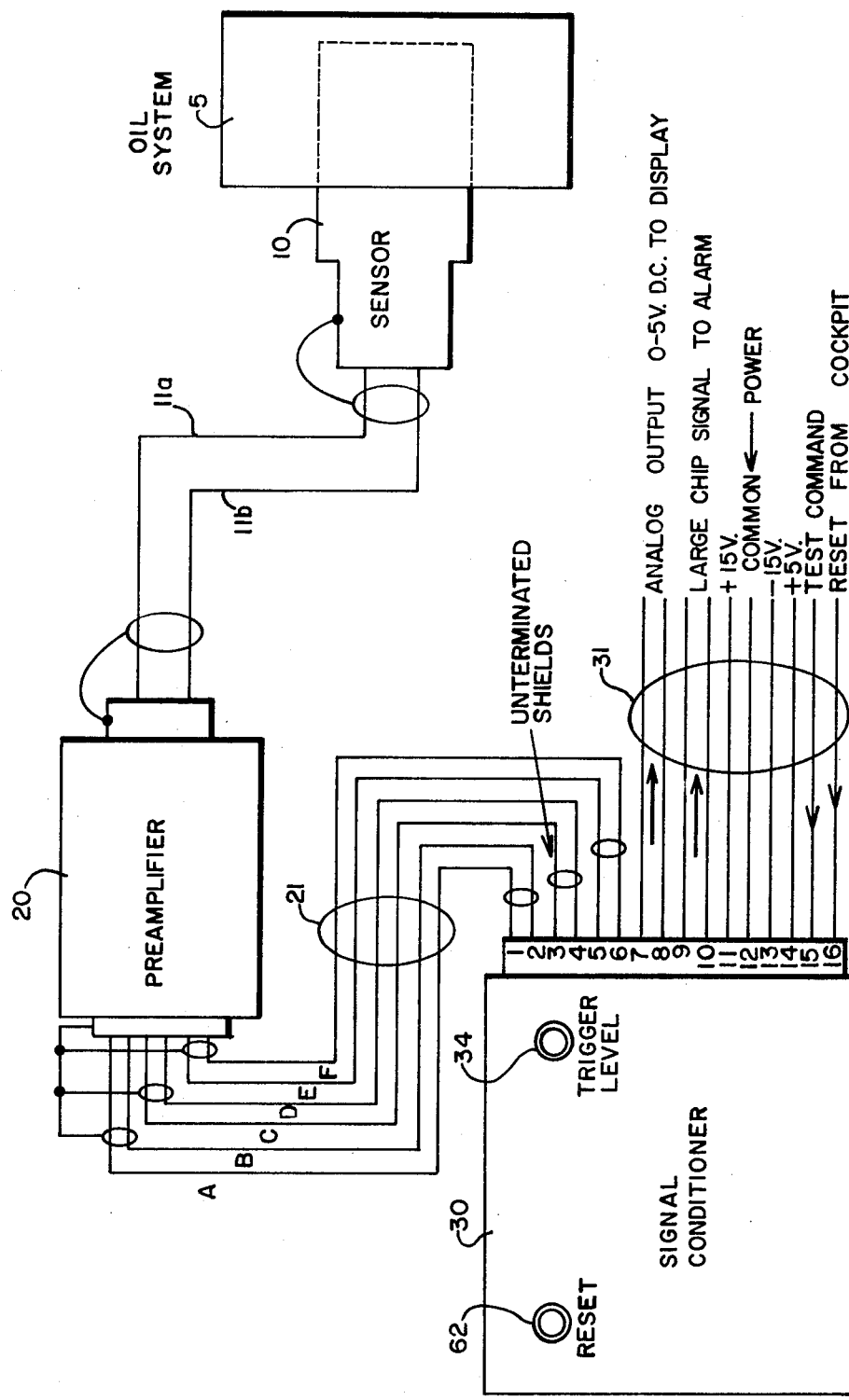
FIG. 1 is a block diagram of a debris monitoring system according to the present invention, showing one sensor.

Referring now to FIG. 1 a block diagram of the overall system is shown. This shows an oil circulation system 5 containing a magnetic sensor 10, which is connected by a sensor cable 11 to a preamplifier 20. This, in turn is connected by second cable 21 to a signal conditioner 30 which acts to discriminate against unwanted signals (such as those from vibration and normal fuzz), detect "large" particles, accumulate total mass data and generate various output signals of interest. These outputs are fed via third cable 31 to one or more outputs or displays (not shown) in the helicopter or aircraft cockpit. These displays can be conventional audio alarms, visual warning lights, or volt meters, either analog or preferably, digital. Such display items are well known and readily available at a reasonable cost.

In actual practice, more than one sensor system may be used in a helicopter to monitor such diverse areas as the rotor gear box and the engine oil sumps for particle accumulations. As currently configured, each system would require an independent sensor, preamplifier and signal conditioner to present its data. However, the several systems need not be totally isolated from each other and can operate from a suitably decoupled common power supply with the outputs multiplexed to a common display. Techniques for simply accomplishing these requirements are well known in the art.

Lastly, the system provides a periodic test command or signal to test the functionality of the system which, as shown, originates from a computer. The computer per se is not part of the invention as described but rather is a reference to an on-board computer found in many aircraft including military helicopters. Where such a computer is not available such a signal can easily be generated by a clocked flip-flop or similar integrated timing means within the basic system structure. The computer can also be used to monitor rate of accumulation data by determining the particulate mass (as determined herein) per unit time ratio, and activating an alarm if this exceeds a preset programmed value.

The following paragraphs describe in detail the preferred embodiment of a single sensor ferrous particle monitoring system according to the present invention and the procedure for using it. However, it should be understood that this description is not intended to limit the invention to either the embodiment or procedure described. On the contrary it is intended to cover all alternatives, modifications and equivalents as may be included within the sphere and scope of the invention defined by the appended claims.

SENSOR

Figure 2A:
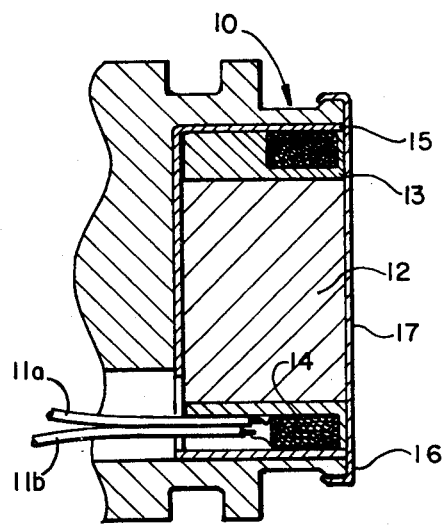
FIGS. 2a and 2b show cross sectional views of two types of sensor heads as shown in FIG. 1.

Referring now to FIG. 2a we see a view of a sensor 10 for this system. As shown it consists essentially of cylindrical permanent magnet 12 set concentrically into the bobbin 13 of a spool of coiled wire 14 which acts as a pickup coil. This combination is further fitted into a cylindrical magnetic steel shroud 15 open ended at the top. The top is fitted with a thin nonmagnetic steel cap 16, the outer top side of which then becomes the collection surface 17 for the debris particles. The turns of wire on the spool are concentrated around the top pole 18 of the magnet which is in close proximity to the cap 16. In this arrangement the lines of flux produced by magnet 12 couple through the windings of the coil into and emanate from top cap 16 to create an attractive magnetic zone in the vicinity of the collection surface. When a ferrous particle enters the magnetic zone and is captured on surface 17 it acts to disturb the lines of magnetic flux so as to induce a voltage in pickup coil 14, said voltage being transmitted down lines 11a and 11b in sensor cable 11 to preamplifier 20. After the captured particle comes to rest on surface 17 and the dynamic disturbance of the flux pattern is over, the transmitted voltage quickly falls to zero. The sensor thus acts as a random pulse generator with respect to the arrival and capture of ferrous particles.

Figure 2B:
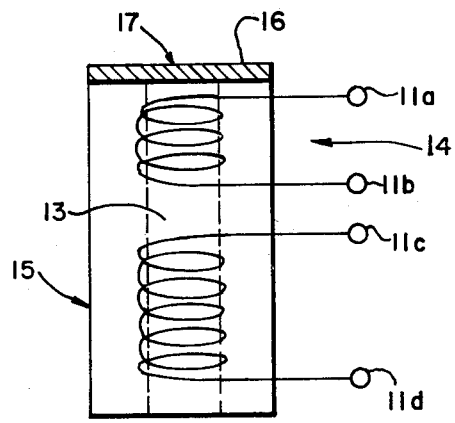

Permanent magnet 12 and coil 14 are not crucial to the operation of the sensor, and other methods of generating the magnetic field can be used. Thus, FIG. 2b shows an alternative approach. In the embodiment shown in FIG. 2b magnet 12 is replaced by an electromagnet consisting of a soft iron core 13 which in turn is energized by a power coil 15 connected to a separate power supply (not shown) by lines 11c and 11d in cable 11. This presents a self cleaning advantage for some applications in that the debris particles will tend to fall off of collection surface 17 when system power is off. The freed particles can then be trapped by a second permanent magnet (not shown) which can be removed for inspection without the necessity of shutting down either the helicopter engine or the detector system.

Figure 3:
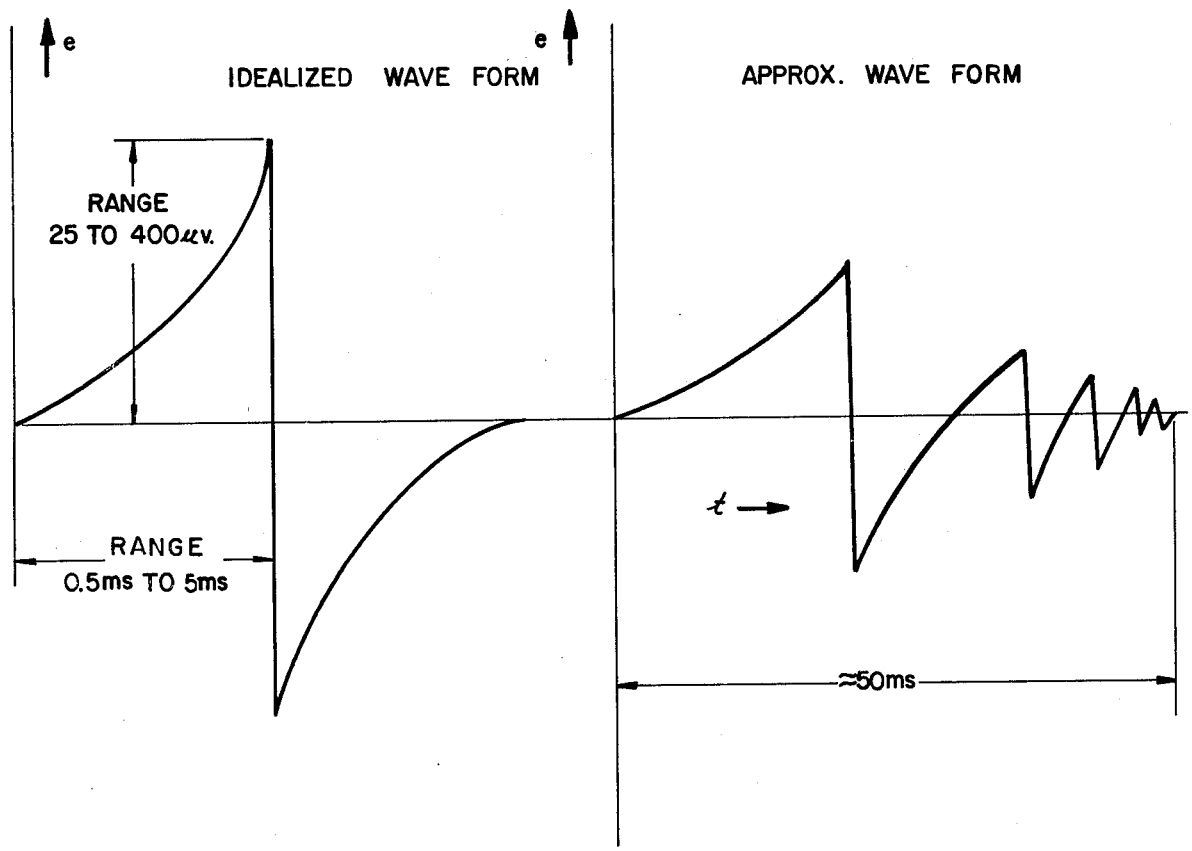
FIG. 3 is a drawing of the wave form produced by the sensor when a ferrous chip or particle is captured.

FIG. 3 shows representations of both an ideal pulse which should be produced under such circumstances and the general characteristics of the pulse actually produced by the sensor when subjected to disturbances by ferrous particles of the sizes of interest. In general these particles range from 150 to 750 microns in size. The absolute magnitude of the pulse amplitude is also affected by such particle parameters as velocity, permeability and path of travel as well as the strength of the magnetic field generated by magnet 12.

PREAMPLIFIER

Figure 4:
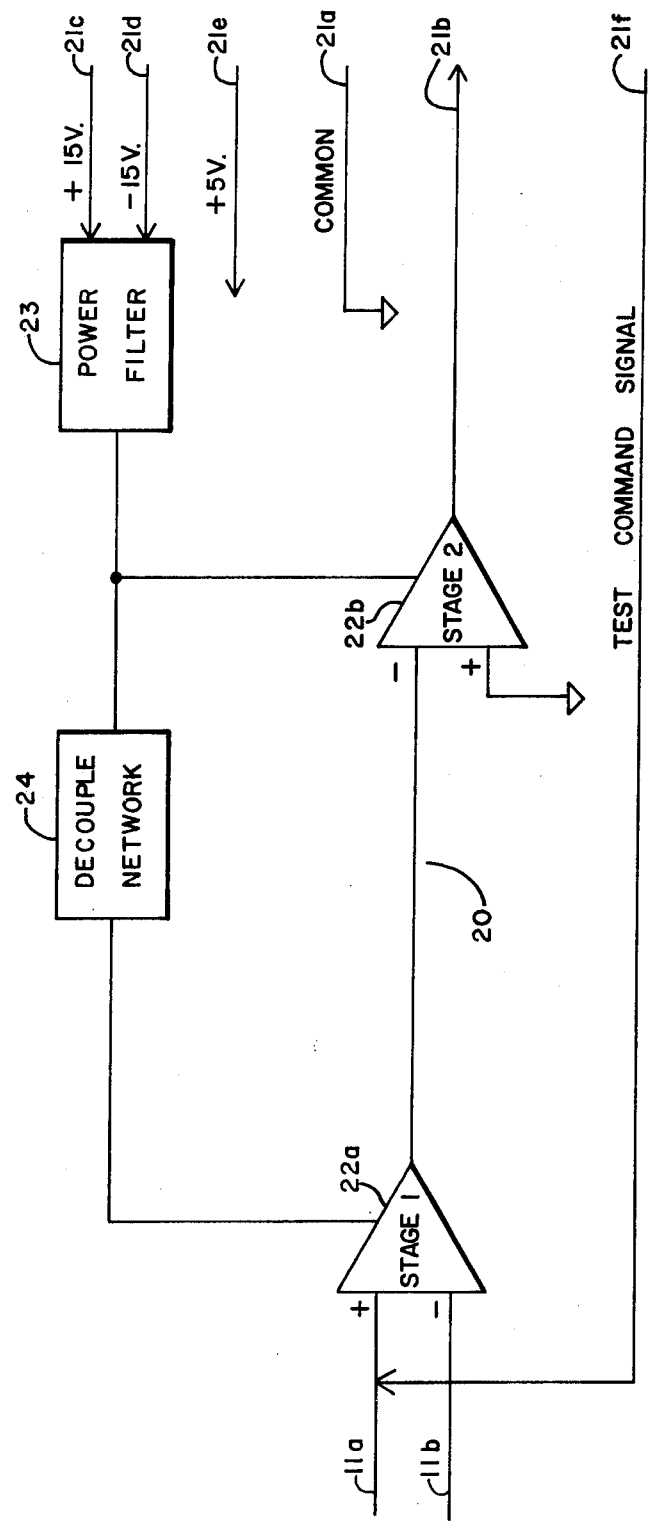
FIG. 4 is a block diagram of the signal preamplifier shown in FIG. 1.

The essentials of preamplifier 20 are shown in FIG. 4. It consists of an input cable 11 from the sensor and output cable 21 to signal conditioner 30 and two stages of amplification 22a and 22b. In the preferred embodiment the first stage 22a has a balanced differential noninverting input to minimize common mode noise pickup by sensor output cable 11 (which can be as much as 20 feet long). Input stage feedback resistor values are chosen not only to limit the band width to about 2 kilohertz (to accomodate the rise times of the debris particle pulses generated) but also to reject any high frequency transients which might originate from electronic components in the vicinity of the system. As configured in FIG. 2a the output impedance of sensor 10 is generally only about 100 ohms, so the input impedance of the preamplifier should also be modest to reduce the sensitivity to noise.

The second stage 22b is an AC coupled single ended inverting amplifier. Because of the relatively high gain involved the $\pm 15$ volt power supply in lines 21c and 21d of cable 21 after passing through power filter 23 should be decoupled by a network 24 between the two stages to minimize stray noise pickup from these lines. The output impedance from stage 22b is 75 ohms and is sufficiently low to drive a shielded pair cable (lines 21a and 21b of cable 21) up to 100 feet long to the input of the signal conditioner 30. To provide the necessary gain for such a cable length a feedback resistance of about 820K ohms should be used. The test signal shown as line 21f in cable 21 is derived from the onboard computer (not shown).

SIGNAL CONDITIONER

Figure 5:
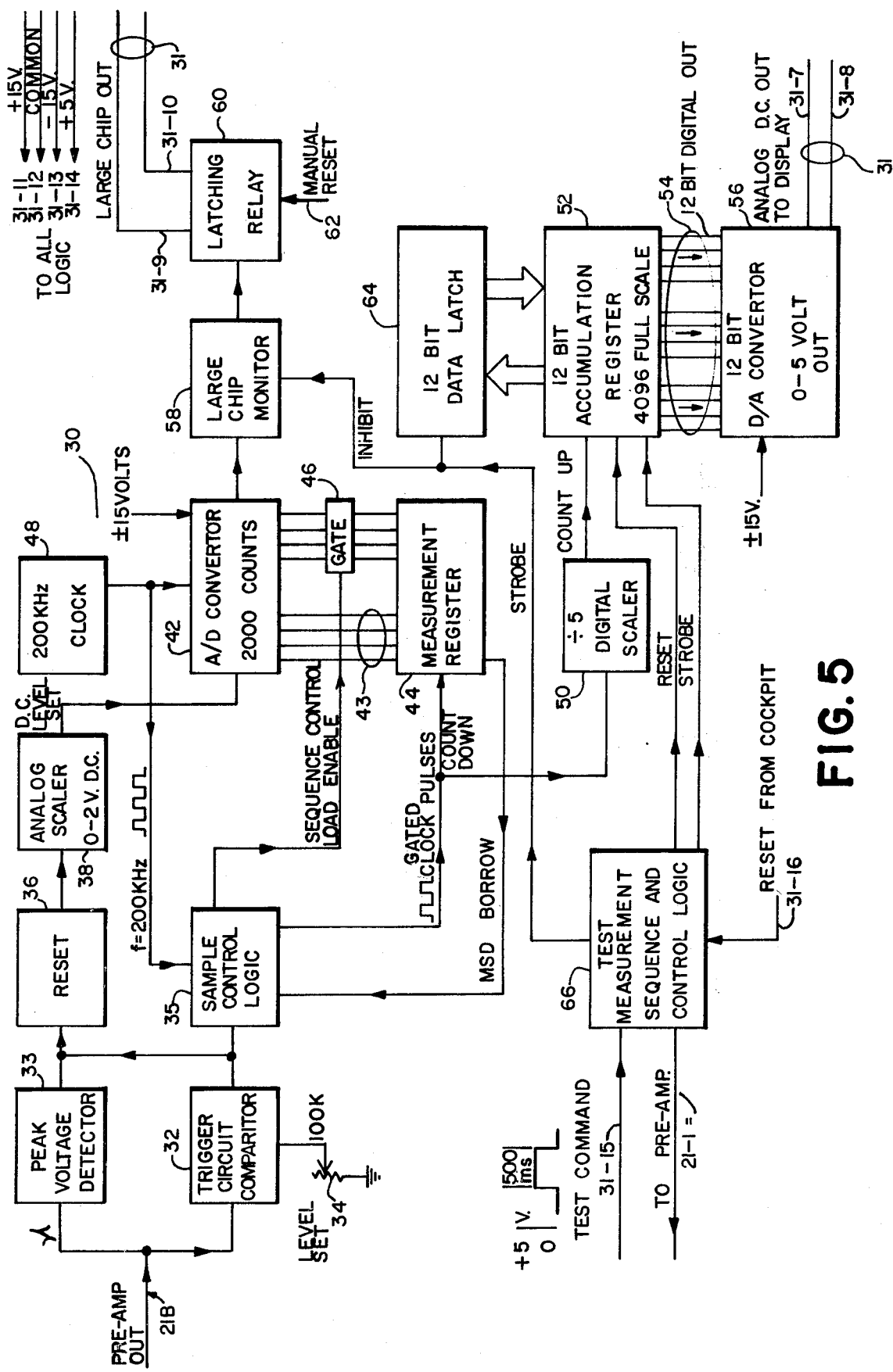
FIG. 5 is a block diagram of the signal conditioner shown in FIG. 1.

Referring now to FIG. 5 we see a block diagram of signal conditioner 30 whose operation will subsequently be described. The amplified pulses coming down input 21b from preamplifier 20 are divided and fed into both a comparator circuit 32 and a pulse peak amplitude circuit 33. The threshold level of the comparator is normally set by potentiometer 34 to tigger the circuit only when the particle mass just captured is above that of the smallest particle which it is desired to detect and recor (100+ microns). By so doing signals from fuzz particles can be effectively screened out and ignored.

When the comparator circuit triggers, it enables sample control logic 35 and also releases reset 36 on the peak detection circuit. This in turn allows analog scaler 38, containing a charging compacitor to charge up to and store the magnitude of the peak value of the pulse just received. A very high impedance voltage divider across this capacitor establishes a 0 to 2 DC voltage discharge which is input to analog to digital (A/D) convertor 42. A/D convertor 42 acts to measure this voltage and convert it internally to a binary coded decimal (BCD) digital output. The convertor then serially presents these data on four output lines 43 (1248 BCD encoded) sequentially from the most significant digit ("MSD") to the least significant digit ("LSD") to measurement register 44 into which they are loaded in parallel. The sequence of the actual loading operation into the register is controlled by gate 46 which is enabled by sample control logic 35 when the A/D conversion is completed. This can count up serially from 0 to as high as 15 (in binary) on its four output lines. After the LSD is entered the control logic then closes the gate and simultaneously acts to feed pulses from clock 48 into both the countdown control of measurement register 44 and, through divide by 5 digital scaler 50, into accumulation register 52. This counts up as the measurement register counts down and acts to create a scaled binary equivalent of the BCD digital value. The countdown is concluded when the measurement register reaches zero. At that point a borrow signal appears from the most significant digit which acts to shut off the clock gate. When this happens the accumulation register input is also closed thus storing the binary value for the pulse amplitude received. As a result of the countdown the measurement register is cleared and is now able to receive and act upon the next piece of data which will come out of the A/D convertor. The accumulation register, however, is not cleared and therefore contains the total value for all of the pieces of data which have been received and accepted. This figure (in binary) can be fed through 12 bit output line 54 directly into a digital output device but is more easily handled in analog (D/A) convertor 56. This produces a DC output voltage of 0 to 5 volts full scale proportional to the digital input from the accumulation register which is then fed through lines 7 and 8 of cable 31 to the display (not shown) in the cockpit. The above process is repeated for subsequent debris particles hence the accumulation register is always updated to totalize the debris particles accumulated and the analog output always follows the increasing digital input. The output display in the cockpit can be read on either a conventional analog panel meter or a standard 5 or 6 figure digital volt meter.

Also associated with A/D convertor 42 is a large chip decode circuit 58 which is activated if the measured value for any one chip exceeds a preset value of 350 microns. This acts to close a latched contact relay 60 which in turn puts out a "large chip" signal to the cockpit through lines 9 and 10 of cable 31. Once activated this relay can only be reset to the unlatched (open) position by depressing a manual reset button 62, by turning the system power off and then back on again, or by an external recycle generated from the computer. The output from the large chip detector will normally be used to activate an audio/visual alarm in the cockpit (not shown) to alert the pilot to the situation. Continued receipt of such signals would provide a positive indication of the existence of particles indicating accelerated crack growth as differentiated from a random sliver of relatively minor significance. Such an occurrence would then be a clear warning that the rate of accumulation is accelerated and that immediate maintenance is needed to prevent castastrophic failure in the near future.

SYSTEM TEST

With respect to the periodic test command signal from the on-board computer or a similar device the following sequence take place:

1. When the leading edge of the test command signal is sensed, a strobe pulse is generated in test measurement sequence control logic 66 which enables the accumulation register to transfer its contents, in parallel, to the 12 bit data latches 64 for storage while the large chip memory circuit 58 is simultaneously inhibited.

2. A reset pulse generated by the sequence control logic then resets the contents of the accumulation register to zero. This also results in the output of D/A convertor 56 reading out a zero value into the display.

3. A test pulse of known amplitude and time is next injected into the input of preamplifier 10. The measurement and transfer process described above for "real" pulses then takes place and the output of the D/A convertor observed in the cockpit. The value seen is a measure of the proper functioning of the test system independent of any signal originated by debris particles captured by the system. This value must fall within preset and known limits to signify satisfactory operation of the system.

4. On the falling edge of the test command signal the test signal is removed and the stored digital contents in latches 64 are then parallel loaded back into the accumulation register 52. The inhibit is also removed from large chip memory circuit 58 and the output of D/A convertor 56 assumes the value it held prior to the test command. The system is therefore ready for further measurement and accumulation and will do so until the next test command signal is received.

Thus it is apparent that there has been provided, in accordance with the invention, a lubricating oil debris monitoring system that fully satisfies the objects and advantages set forth above.

Although the present invention has been described with reference to the particular embodiments herein set forth, it is understood that the present disclosure has been made only by way of example and that numerous changes in the details of construction may be resorted to without departing from the spirit and scope of the invention. Thus, the scope of the invention should not be limited by the foregoing specification, but rather only by the scope of the claims appended hereto.

What is claimed is:

1. An apparatus for monitoring the quantity of ferrous particulate debris in oil and hydraulic fluid systems comprising:
    a magnetic sensor including a magnetic field to attract and capture a plurality of ferrous particles and a pulse generating means which generates a pulse to signal the capture and mass of said particles;
    a preamplifier to amplify said pulses operatively connected to said sensor;
    signal conditioning means to evaluate said amplified pulses and provide output signals which are a function of the mass of said particles, operatively connected to said preamplifier; and
    display means operatively connected to said conditioning means to provide an audio/visual output of said proportionate signals.

2. The apparatus of claim 1 wherein said conditioning means includes, self testing means to provide a periodic analysis of system functionality, and adjustment means to modify the output on said display means.

3. The apparatus of claim 2 wherein said pulse generating means further comprises:
    a coil adapted to be contained within and coupled to the magnetic field of said sensor; and
    a nonmagnetic top plate operably adapted to act as a receiver and retainer for said captured particles.

4. The sensor of claim 3 wherein said magnetic field is generated by a permanent magnet.

5. The sensor of claim 3 wherein said magnetic field is generated by an electromagnet including a soft iron core.

6. The apparatus according to claim 5 wherein the self testing means further comprises means for deactivating said sensor and storing said accumulated mass signal and is further adapted to inject a test signal of known amplitude and duration for processing said test signal through said amplifier and said signal conditioner for display to the operator and being further adapted to increase or decrease overall system gain by said adjustment means.

7. The apparatus of claims 1 or 2 wherein said conditioning means further includes:
discrimination means to screen out signals from normal wear particles in the fluid system;
large chip detector monitor means to provide alarm signals when very large ferrous particles are captured;
accumulation means adapted to store and provide an output signal proportional to the total mass of said particles which have produced signals sufficient to pass through said discrimination means; and
output means adaptable to both analog and digital display.

8. The apparatus of claim 7 wherein the signal conditioner discrimination means further comprises a peak voltage detector and a comparator trigger.

9. The apparatus of claim 7 wherein the signal conditioner large chip monitor means is operably connected to a manually resetable latching relay, the output of which, when activated and latched, being a signal to an alarm.

10. The apparatus of claim 9 wherein the signal conditioner accumulation means is further adapted to scale said output signals for direct display of the accumulated mass of said particles.

11. The apparatus of claim 10 wherein said display means further comprises a volt meter wherein said scaled signals are directly presented as the mass of said accumulated particles.

12. The apparatus of claim 10 further comprising means to measure the time between occurances of said output signals so that the rate of partical capture can be determined and further comprising alarm means to warn the operator when the rate exceedes a preset limit.

13. The method of detecting and analyzing ferrous particles in a circulating lubricating oil system comprising:
capturing the particles by a magnet;
generating pulses in a coupled concentric coil around said magnet as said paricles are drawn towards a capture plate on top of said magnet;
amplifying said pulses, measuring their amplitude and discriminating said pulses to only pass signals from said particles which are indicative of abnormal wear;
triggering an alarm when a mass of any given particles is over a preset limit;
converting the analog amplitudes of said discriminated pulses to equivalent digital values, and accumulating said digital values to provide a digital signal equal to the total mass of abnormal particles which have been captured; and
displaying the value of said total mass of abnormal particles to an operator for corrective action if necessary.

* * * * *